United States Patent
Alfano et al.

(10) Patent No.: US 10,733,729 B2
(45) Date of Patent: Aug. 4, 2020

(54) METHOD FOR IMAGING BIOLOGICAL TISSUE USING POLARIZED MAJORANA PHOTONS

(71) Applicant: Research Foundation of the City University of New York, New York, NY (US)

(72) Inventors: Robert R. Alfano, Bronx, NY (US); Sandra Mamani, New York, NY (US); Lingyan Shi, New York, NY (US)

(*) Notice: Subject to any disclaimer, the term of this patent is extended or adjusted under 35 U.S.C. 154(b) by 0 days.

(21) Appl. No.: 16/573,521

(22) Filed: Sep. 17, 2019

(65) Prior Publication Data

US 2020/0090329 A1 Mar. 19, 2020

Related U.S. Application Data (60) Provisional application No. 62/732,378, filed on Sep. 17, 2018.

(51) Int. Cl.
*G06T 7/00* (2017.01)
*G01N 33/483* (2006.01)
*G01N 21/21* (2006.01)
*G01J 4/00* (2006.01)

(52) U.S. Cl.
CPC ........... *G06T 7/0012* (2013.01); *G01N 21/21* (2013.01); *G01N 33/4833* (2013.01); *G01J 2004/001* (2013.01); *G01N 2021/216* (2013.01)

(58) Field of Classification Search
CPC ...... G01N 21/17; G01N 21/453; G01N 21/21; G01N 21/23; G01N 24/00; G01N 33/483; G01N 33/4833; G01N 33/48; G01N 2021/1765; G01N 2021/216; G01N 2021/218; G01J 2009/002; G01J 2009/004; G01J 4/00; G01J 4/02; G01J 4/04; G01J 9/00; G01J 2004/001; G01J 2004/002; G01J 2004/005; G02B 21/002; G06T 7/0012
USPC .................................................. 356/364–370
See application file for complete search history.

(56) References Cited

U.S. PATENT DOCUMENTS

| | | | | |
|---|---|---|---|---|
| 8,111,957 | B2* | 2/2012 | Alfano | G02B 6/024 385/28 |
| 9,134,300 | B2* | 9/2015 | Danias | A61B 3/10 |
| 9,350,977 | B1* | 5/2016 | Prasad | G02B 27/0075 |
| 9,823,486 | B2* | 11/2017 | Prasad | G02B 27/0075 |
| 10,156,669 | B2* | 12/2018 | Beresna | G02B 5/1809 |
| 10,209,192 | B2* | 2/2019 | Ashrafi | G01N 21/6428 |
| 10,401,294 | B2* | 9/2019 | Alfano | G02B 21/0036 |
| 2007/0115551 | A1* | 5/2007 | Spilman | G02B 27/286 359/489.07 |
| 2019/0290100 | A1* | 9/2019 | Ramachandran | G02B 6/02195 |

(Continued)

OTHER PUBLICATIONS

Lalithambigai, K. et al., "Formation of multiple focal spots using a high NA lens with a complex spiral phase mask," 2014, IOP Publishing, Royal Swedish Academy of Sciences, Physica Scripta, 89, 075501 (7 pp) (Year: 2014).*

(Continued)

*Primary Examiner* — Gordon J Stock, Jr.

(57) ABSTRACT

Majorana photons are transmitted through a biological tissue sample to image the tissue. The Majorana photons have a circular polarization, a radial polarization or an azimuthal polarization. The transmitted photons are processed to produce a digital image of the biological tissue sample.

2 Claims, 5 Drawing Sheets

(56) References Cited

U.S. PATENT DOCUMENTS

2019/0393963 A1* 12/2019 Shi .................. H04B 10/556

OTHER PUBLICATIONS

Man, Zhongsheng et al., "Focusing properties of arbitrary optical fields combining spiral phase and cylindrically symmetric state of polarization," May 24, 2018, Journal of the Optical Society of America A, vol. 35, No. 6, pp. 1014-1020 (Year: 2018).*

Shi, Lingyan et al., "Propagation of Laguerre-Gaussian vortex beams through mouse brain tissue," Feb. 27, 2017, Proc. SPIE 10120, Complex Light and Optical Forces XI, 101201B, 3 pages. (Year: 2017).*

Wang, Tingting et al., "Focusing properties of cylindrical vector vortex beams with high numerical aperture objective," 2013, Optik 124, pp. 4762-4765. (Year: 2013).*

* cited by examiner

METHOD FOR IMAGING BIOLOGICAL TISSUE USING POLARIZED MAJORANA PHOTONS

CROSS-REFERENCE TO RELATED APPLICATIONS

This application claims priority to and is a non-provisional of U.S. Patent Application 62/732,378 (filed Sep. 17, 2018), the entirety of which is incorporated herein by reference.

BACKGROUND OF THE INVENTION

Photons possess novel salient properties such as polarization, wavelength, coherence, speed, and spatial modes, which can play an important role for propagation and imaging in scattering media. Structured vector light spatial mode is an active research topic in various fields in classical and quantum entanglement applications. Photons can have unique vector properties which show that certain photons can be entangled locally and non-locally, separable and non-separable on wave front; can also posses spin angular momentum (SAM) and orbital angular momentum (OAM).

Due to inhomogeneous make up of tissue from particles and structure, biological tissues are highly scattering media. In this case, the wavelength plays a key role for biological media the scattering reduces as wavelength enters the NIR (650 nm to 950 nm) and in SWIR (1000 nm to 2500 nm). The optimum window in SWIR for deep imaging is the golden window (1600 to 1870 nm) in the brain.

Moreover, photon polarization plays an important role in tissues since it can affect the depth at which the beam travels. For example, it is known that circular polarized light goes deeper than linear polarized light in scattering media. Depending on scattering unit size, the polarization retains optical memory. A Laguerre-Gaussian beam (LG beam), which is a vortex beam, can carry different types of polarization (linear, circular, radial and azimuthal) along with a phase front characterized by an orbital angular momentum (OAM) of 1 value and spin angular momentum (SAM) $S=+/-1$. Light beams with spatially inhomogeneous profile of polarization are referred to as vector beams. The various spatial modes, such as the radial and azimuthal, have non-separable parts for circular polarization and OAM. The combination of polarization and spatial modes leads to special class of photons. These quasi particles are the basis proposed here as Majorana photons—where photons and antiphotons are the same.

The key characteristic of vector beams such as radial and azimuthal combines polarization and spatial modes, which are non-separable and are locally entangled. The focus of these beams have a longitudinal field. Moreover, the characteristic of non-separability in vector beams is of great interest not just in optical imaging but in optical communication and computers as well since its polarization degree of freedom and spatial mode are being explored to encode information. There are two special vector beams, radial and azimuthal; these two are a mixture of OAM and circular polarization; and are introduced here as Majorana modes and interaction in tissue for the first time. There is a search on for special quasi particles for storage and more stable for qubits that are less effected by interference and by the environment to reduce de-coherence effects and scattering.

Majorana can exist not only as fermions but also as bosons coincide of particle and antiparticle such as gravitons, photons and possible the neutrino, as they must be their own anti-particle and have opposite charges and same masses. Majorana only works for neutral particles. Charge and neutral particles have antiparticles; that is an electron with charge $-e$, so its antiparticle (the positron has charge of $+e$). These can not constitute a Majorana particle. However, the neutrino can fit, being a Majorana. Some have proposed bosons can be photons. Photons have no charge, the Majorana involves not only spin angular momentum but the vector sum of total angular momentum J, with OAM(l). Because of the transverse nature of electric (E) and magnetic (B) fields, the photon has zero rest mass. However, if special photons have a longitudinal field then the photon may have a small mass (Procar) on order of 10-49 gm. Majorana photons have both chiral twists. The key Majorana characteristic wave function feature is being its own anti-particle, where $\psi=\psi^*$, being Hermitian. This Majorana as qubit of this type is topological which means its property remains almost the same regardless of the scattering exchange and the path taken in environment such as scattering. The Fourier transform of a pulse at $\omega_o$ of duration $\tau_p$ in the time domain transforms mathematically into frequency domain signals centered at $\omega_o$ and $-\omega_o$. Typically in an Optics course, one can drop the negative frequency $-\omega_o$ as being physically not real. However, this is not totally correct. The negative frequencies of photons mean negative energy $E=h\nu$ exactly what Dirac found when he completed solving relativistic quantum mechanics equations and found anti-electrons and anti-particles. Later, positron was found. Experimentally Ettore Majorara proposed a neutrino as being a particle being its own anti particle. Majorana neutrinos have the property that the neutrino and antineutrino could be distinguished only by chirality. If experiments observe a difference between the neutrino and antineutrino could simply be due to one particle with two possible chiralities. It is still not yet known whether neutrinos are Majorana or Dirac particles; photons do possess chirality in from of vector beams.

The discussion above is merely provided for general background information and is not intended to be used as an aid in determining the scope of the claimed subject matter.

SUMMARY

Majorana photons are transmitted through a biological tissue sample to image the tissue. The Majorana photons have a circular polarization, a radial polarization or an azimuthal polarization. The transmitted photons are processed to produce a digital image of the biological tissue sample.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This disclosure pertains to certain vector class of photons being a Majorana, a combination of particle and antiparticles such these photon modes are defined and attributed as Majorana boson photons stated as shown to be $\psi=\psi^*$. The photon and the anti-photon are identical. Some beam possesses both right and left circular polarization.

This disclosure focuses on the transmission of these Majorana LG vector vortex beams through mouse brain tissue. The regimes that are disclosed are in the ballistic ($z<l_{tr}$) and diffusive ($z>l_{tr}$) regions, where z is the thickness of the turbid media and $l_{tr}$ is the transport mean free path. Different types of polarizations at different special locations of the mouse brain at various thicknesses are investigated to demonstrate the role of Majorana photons in potentially improving imaging with higher flux of photons in the classical limit. The radial and azimuthal beams are defined to be Majorana-like photons.

The brain is a biological tissue made up of neurons and axons in tree-like structure. Neurons are organized by integrated networks of proteins polymers, which are considered a chiral media. This chiral media will interact with the electromagnetic field of light by changing its state of polarization; this effect makes the brain a chiral bioplasma. Structured vector light is expected to interact with chiral matter by coupling with electric dipole, magnetic dipole and quadrupole moments and transitions from Fermi Golden Rule. The underlying unique and complex structure and properties makes the brain a "smart tissue"; due to this heterogeneity in the brain, different regions could show dissimilar effects. Electric quadrupole interactions enable the twisted light to twist more with a wavelength to be involved with local electronic transitions. Therefore, we decided to focus on main brain regions such as the cortex, white matter and hippocampus. White and grey (cortex and hippocampus) matter are considered major regions of the central nervous system. These are regions mainly affected by neurodegenerative diseases such as Alzheimer's and multiple sclerosis among others.

In the disclosed experiment, these brain regions are examined to determine whether there are special maze pathways in brain tissue for photons to propagate as radial and azimuthal Majorana LG vortex for J beams. The polarization and OAM value l are changed for each localized spatial region. The goals are to observe if there is a direct proportionality between the OAM l and the transmission, and chiroptical interactions between a targeted region in the brain and each polarization used. Chiroptical effects involve interplay of chirality of molecular, and electromagnetic radiation to produce energy shifts to the handedness of circular polarized photons such as circular dichroism in solids, liquids and biofluids.

Prior studies have been done where mouse brain transmission with LG was also analyzed for linear polarized light with no classical entanglement. No transmission difference effect was observed for linear polarization (LP) on OAM (t). Here, the polarized states are further expanded to include classical entangled beams with circular, radial, and azimuthal polarization for OAM of LG beams for Majorana. One can expect that circular polarization and entangled light beams will affect the photons absorption rates. The use of classical entanglement is that it operates locally and uses a high flux of photons in contrast to quantum entanglement that uses a single low photon number non-locally.

Majorana and other states of polarization and spatial modes of photons: Vector beams are spatial modes with varying states of polarization. Radial polarized (RP) and azimuthal polarized (AP) modes can produce stronger longitudinal electric and magnetic field components upon focusing. RP can also generate smaller spot size upon focusing by a high NA objective lens to form imaging in nano scale. Most importantly, RP and AP are nonseparable beams (mixed states) in space and polarization, being classically entangled. These modes are defined and attributed as Majorana boson photons as shown to be $\psi=\psi^*$.

The following represents the four polarization states in Dirac notation and Jones vector. Equation (1) is a linear polarization, which is a state representation of right and left circular polarization.

$$|LP\rangle=|RH\rangle+|LH\rangle \qquad (1)$$

Equation (1) contains polarization spinning together in opposite directions as RH-CP and LH-CP.

Circular polarization can be written in a more general form as shown in Eq. (2) as a pure state:

$$|CP\rangle = \cos\phi |x\rangle \pm \sin\phi e^{i\delta}|y\rangle \quad (2)$$

where $\phi$ represents the azimuthal phase at $\pi/4$ with respect to the x-axis and $\delta$, which is the complex phase taken at $\pi/2$, $|+\rangle$ and $|-\rangle$ are two general eigenvector states, which represent two column vectors $$\begin{pmatrix} 1 \\ 0 \end{pmatrix} \text{ and } \begin{pmatrix} 0 \\ 1 \end{pmatrix}.$$

Equation (3) represents right-handed circular polarization:

$$|RH\rangle = \frac{1}{\sqrt{2}}\begin{pmatrix} 1 \\ -i \end{pmatrix} = = \frac{1}{\sqrt{2}}[|+\rangle - i|-\rangle] \quad (3)$$

Equation (4) represents left-handed circular polarization:

$$|LH\rangle = \frac{1}{\sqrt{2}}\begin{pmatrix} 1 \\ i \end{pmatrix} = = \frac{1}{\sqrt{2}}[|+\rangle - i|-\rangle] \quad (4)$$

where $|RH\rangle^* = |LH\rangle$.

Laguerre-Gaussian beams with circular polarization (pure states) are represented by Eq. (5):

$$|l\rangle|RH\rangle; |-l\rangle|RH\rangle; \text{ and } |l\rangle|LH\rangle; |-l\rangle|LH\rangle \quad (5)$$

where l represents the OAM value.

Radial polarized beam shows the mixed of Majorana. Equation (6) shows radial polarization (classical entangled local state) with spatial and polarization:

$$|RP\rangle = \frac{1}{\sqrt{2}}\begin{pmatrix} \cos\phi \\ \sin\phi \end{pmatrix} \rightarrow$$

$$\frac{1}{\sqrt{2}}\left[e^{i\phi}\begin{pmatrix} 1 \\ -i \end{pmatrix} + e^{-i\phi}\begin{pmatrix} 1 \\ i \end{pmatrix}\right] = = \frac{1}{\sqrt{2}}[e^{i\phi}|RH\rangle + e^{-i\phi}|LH\rangle] \quad (6)$$

The notation in Eq. (6) shows that radial polarization is a superposition of two states $|RH\rangle$ and $|LH\rangle$. The exponent is a variation phase and is a unique characteristic of vortex beams. This one proves to be a Majorana photon. Laguerre-Gaussian beams with radial polarization are Majorana photons represented by Eq. (7), which is a mixed of states:

$$|LG_{RP}\rangle \frac{1}{\sqrt{2}}[|-l\rangle|LH\rangle + |l\rangle|RH\rangle] \quad (7)$$

Equation (8) represents azimuthal polarization (classical entangled local mixed state) with spatial and polarization as another Majorana photon:

$$|AP\rangle = \frac{1}{\sqrt{2}}\begin{pmatrix} -\sin\phi \\ \cos\phi \end{pmatrix} \rightarrow \frac{1}{\sqrt{2}}\left[e^{i(\phi+\pi/2)}\begin{pmatrix} 1 \\ -i \end{pmatrix} + e^{-i(\phi+\pi/2)}\begin{pmatrix} 1 \\ i \end{pmatrix}\right] = = \quad (8)$$

$$\frac{1}{\sqrt{2}}[e^{i(\phi+\pi/2)}|RH\rangle + e^{-i(\phi+\pi/2)}|LH\rangle]$$

The notation in Eq. (8) shows that azimuthal polarization is also made of a superposition of $|RH\rangle$ and $|LH\rangle$. However, the variation phase has an extra $\pi/2$ phase shift.

Majorana Laguerre-Gaussian beams with azimuthal polarization are represented by Eq. (9), which is a mixed of states:

$$|LG_{AP}\rangle \frac{-i}{\sqrt{2}}[|-l\rangle|LH\rangle - |l\rangle|RH\rangle] \quad (9)$$

Taking the complex conjugate of Eq. (3) and (4) of pure circularly polarized states give the following equations:

$$|RH\rangle^* = |LH\rangle \quad (10)$$

$$|LH\rangle^* = |RH\rangle \quad (11)$$

which shows that Eq. (10) and Eq. (11) are not Majorana. However, taking the complex conjugate of a linear polarization Eq. (1), proves to be a Majorana photon as shown in Eq. (12):

$$|LP\rangle^* = \frac{1}{\sqrt{2}}\left(\begin{pmatrix} 1 \\ i \end{pmatrix} + \begin{pmatrix} 1 \\ -i \end{pmatrix}\right) = |LH\rangle = \frac{1}{\sqrt{2}}\left(\begin{pmatrix} 1 \\ -i \end{pmatrix} + \begin{pmatrix} 1 \\ i \end{pmatrix}\right) \quad (12)$$

Moreover, taking the complex conjugate of vector beams (radial and azimuthal) from Eqs (6) and (9), shown below:

$$|RH\rangle^* = |RP\rangle \quad (13)$$

$$|AP\rangle^* = |AP\rangle \quad (14)$$

proves that Eq. (13) and Eq. (14) follow the Majorana feature of $\psi = \psi^*$, being Hermitian as shown in Eq. (15).

$$C = a + a^\dagger = C^* \quad (15)$$

where a and a-dagger represent the creation and annihilation operators of a Majorana photon.

In addition, radial and azimuthal photons are Majorana quasi photon particles for propagating in biological and condensed scattering media.

The photon can excite electrons causing vibrations, which couple to the media quasi-particles to become a coupled quasi-particle or a polariton depending on how $\omega$ gets close to the resonance frequency $\omega_o$. These quasi-particles commonly become one of the following: optical phonon, exciton, plasmon, and/or magnon-polariton. The dielectric media can be represented by. It is known that photons can couple to plasmons, optical photons, magnons and excitons. The photon excitations became a quasi particle from the interactions and become dressed. Quasi particles can be made up of three sub entities: Holons (charge), Orbitons, and Spinons. A Majorana photon quasi-particle can be split into spin and orbital in OAM and SAM optical beams.

Special paths may exist in the brain for photons to travel through. The brain is very different from other body organs such as the breast, cervix, skin and kidney. It has special tree-like structure with connections of 86 billion neurons and axon branches to store and retrieve information from memory. There are 6 different types of nerve cells in the central nervous system, which are nourished and protected by neuroglia or glial cells (glue like media). The photons enter the brain and travel in this maze, interacting with existing chiral proteins and lipid molecules. There is a possible existence of optical waveguide fiber-like lanes in the brain from microtubules that the photon may take upon exiting. If these classical non-separable structure modes exist in the chiral brain, they would increase the transmission and retain coherence. These special photon quasi-particles can be more transmitted and retain the input characteristics and be entangled with sister photons. We have introduced a new Majorana quasi-particle photon that differs from pure states of CP in the brain.

Material and Methods

Figure 2:
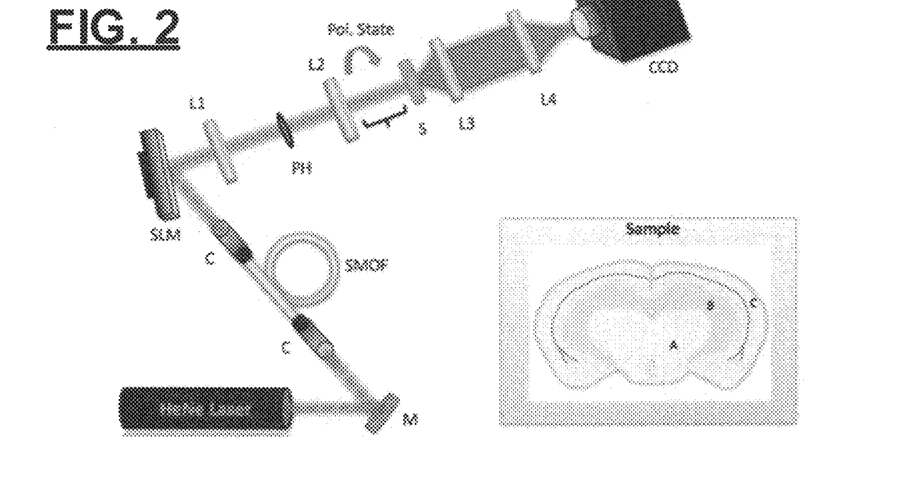
FIG. 2 shows the teneral experimental setup. M, mirror; C, collimator; SMOF, single mode optical fiber; SLM, spatial light modulator; L, lenses; PH, pinhole; Pol. State, four different types of polarization; S, sample; CCD, charge coupled device camera. Sample parts: A—hippocampus; B—white matter; C—cortex.

FIG. 2 shows the experimental setup where a He—Ne laser of 5 mW at 633 nm (horizontally polarized) was used as a light source, focusing onto a single-mode optical fiber (SMOF). The output beam from the optical fiber passed through a collimator and illuminated the spatial light modulator (SLM), which was set at reflection mode. The SLM produced LG beams of different l values that were generated by different forked diffraction patterns. A first lens was used to collimate the first order diffraction through a 400-μm aperture, decreasing the beam's overall exposure to light. A second lens was then used to recollimate the beam. Then the LG beam with specific polarization (see next paragraph) went through a healthy mouse brain sample. Finally, the beam went through a 4l imaging system constituting of two lenses (L3=5 cm, L4=10 cm). A CCD camera detected the output.

To generate the Majorana vector beams with various OAM values, we combined a spatial light modulator (SLM) with a vortex retarder (VR). A SLM is a phase and amplitude modulator that generates vortex beams by inputting computer generated holograms onto the phase of the SLM. A vortex retarder (VR) is a spatially inhomogeneous phase retarder. The one used in the experiment is a l=1 vortex retarder, which is polarization dependent. In the experiment (FIG. 2), the SLM will generate a vortex beam with l value, which will be combined with the VR l value, creating a vortex beam with a total value of OAM. In order to generate the Majorana vector beams with a specific polarization, we fixed the fast axis of the VR to one direction. Then, we sent in different orientation of linear polarization with respect to the axis of the VR. To generate a radially polarized beam, a horizontally polarized beam has to go through a vortex retarder (VR) with respect to its optical axis. To generate an azimuthally polarized beam, a vertically polarized (horizontally polarized beam going into a half wave plate) beam needs to go through the VR with respect to its optical axis. Finally, to generate scalar vortex beams we only used the SLM set at different l values. To generate the circularly polarized light, a linear polarized beam needs to pass through a quarter wave plate at an angle of 45°. Also a half wave plate can be used to generate a left circularly polarized beam.

Brain Tissue Preparation: The brain tissue samples were prepared following the procedures approved by the Institutional Animal Care and Use Committee (IACUC) of the City College of New York under Adrian Contreras. A wild type adult mouse was anesthetized with isoflurane. After the mouse was completely anesthetized (confirmed with no response upon toe pinch), it was decapitated, and the brain was dissected and fixed in 4% paraformaldehyde overnight. The fixed brain was processed with coronal section by using a compresstome (VF300, Precision Instruments, Greenville, N.C.) at two different thicknesses (120 and 600 μm, respectively). The accuracy in tissue slice thickness was ±1 gm.

Figure 1:
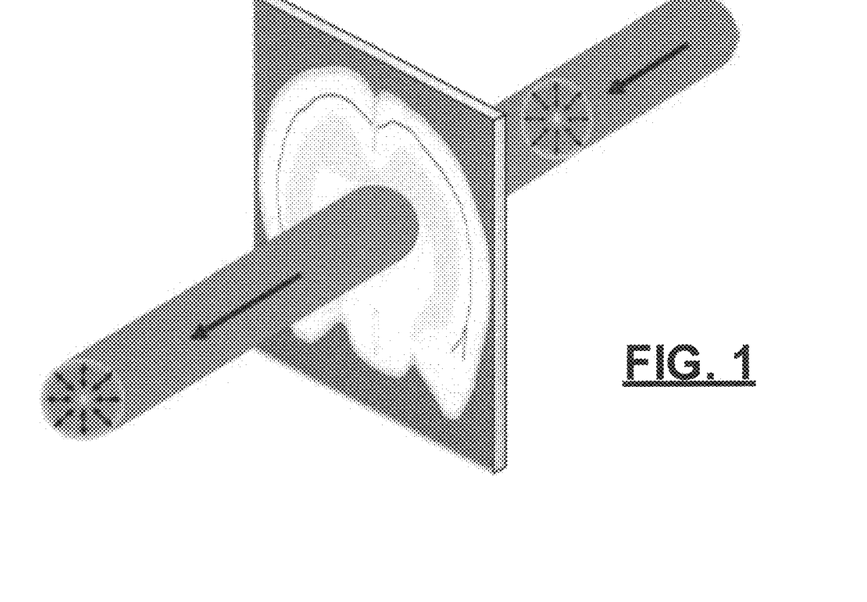
FIG. 1 shows a Majorana radially polarized beam going through a mouse brain slide.

Data collection and analysis: Data was collected for a 120 gm and a 600 gm thick brain tissues for linearly, circularly, radially, and azimuthally polarized beams at different positive l values (l=0, 1, 3, 5, 7), respectively. Also, the size of the OAM beam for each l value was taken into account when sending it through each region of the brain sample. In the 120 gm thick tissue, the LG beam penetrated the cortex, the hippocampus, and white matter. The propagation of the LG beam is considered to be ballistic as the thickness of the sample results in a lack of scattering and interference in the trajectory of the LG beam, creating a straight path of travel 41. In the 600 gm tissue, the LG beam penetrated the cortex and white matter (FIG. 1). The propagation of the LG beam is considered to be diffusive as the increased thickness of the sample results in greater scattering of the LG beam. Furthermore, a reference beam was also measured with no sample to take into account the change of incident light in calculating the transmittance. Finally, the data was analyzed using ImageJ software and by equation (16) as shown below:

$$\text{Transmitted intensity} = \frac{T_s}{T_{ns}} = 10^{-OD} \tag{16}$$

where $T_s$ is transmitted intensity with sample, $T_{ns}$ is the transmitted intensity with no sample.

Results and Discussion

Figure 3:
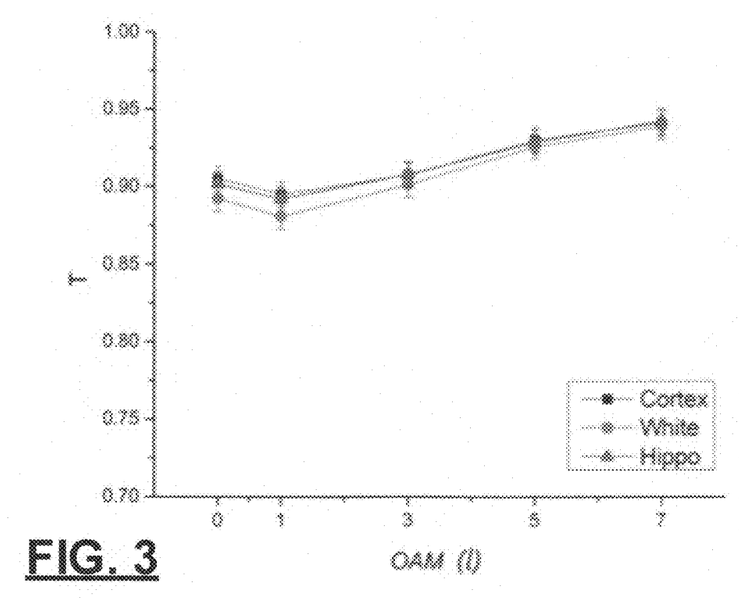
FIG. 3 shows a graph of transmittance (T) through a 120-μm sample as a function of OAM (C) for a collimated horizontally polarized LG beam.

The data in FIG. 3 shows transmission difference between the cortex, white matter and hippocampus for a horizontally polarized collimated LG beam as a function of OAM with the tissue thickness of 120 μm. As shown below the transmittance after l=1 in all targeted areas increases proportionately with l. However, this increase is very small as the transmission ranged is about 6%.

Figure 4:
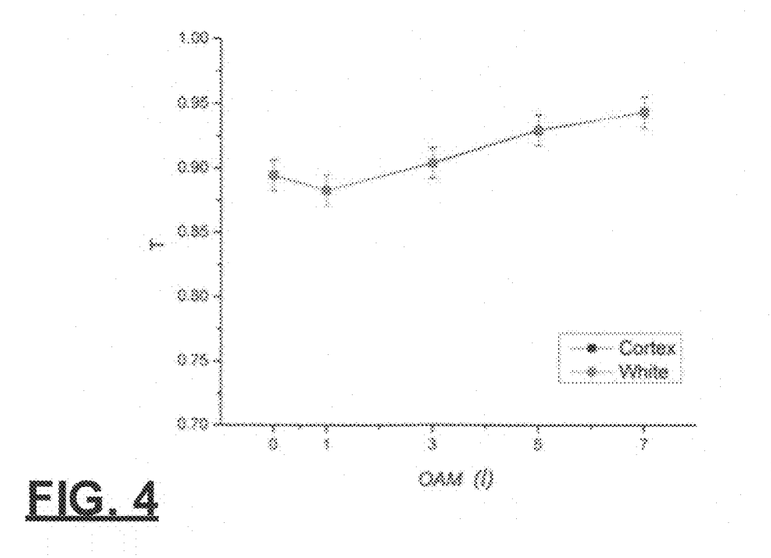
FIG. 4 is a graph of transmittance (T) through a 600-μm sample as a function of OAM (C) for a collimated horizontally polarized LG beam.

FIG. 4 shows transmission difference between the cortex and white matter for a horizontally polarized collimated LG beam as a function of OAM with the tissue thickness of 600 μm. In this case, the transmission range is also about 6%. These results further verify that the relationship between l and transmittance of linearly polarized light through brain tissue is almost insignificant. In addition, this is theoretically proved by Forbes and Andrews that linearly polarization will have little to none chiroptical response from only OAM unlike circular polarization.

Figure 5:
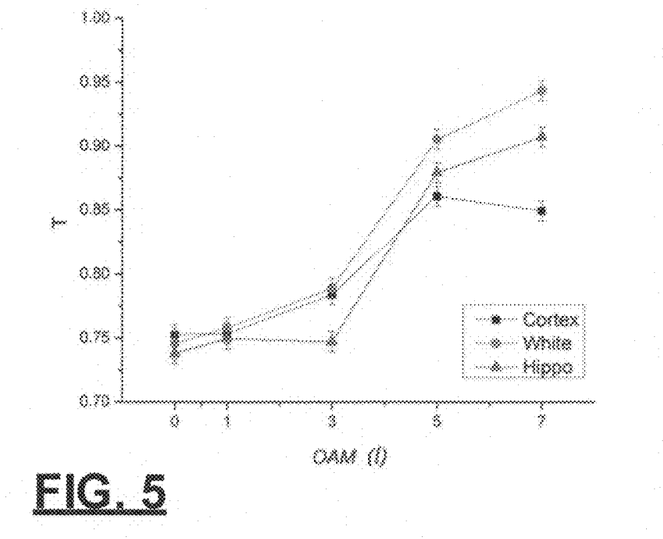
FIG. 5 is a graph of transmittance (T) through a 120-μm sample as a function of OAM (C) for a collimated left circularly polarized LG beam.

FIG. 5 shows transmission difference between the cortex, white matter and hippocampus for a left circularly polarized collimated LG beam as a function of OAM with the tissue thickness of 120 μm. The transmittance of the beam generally increases as l increases in all targeted parts. The sharpest increase in transmittance can be seen from l=3 and above, in which all of the transmittance graphs share a similar curvature. Targeting the white matter consistently yields the highest transmittance, whereas targeting the hippocampus yields the lowest transmittance from l=0 to slightly before l=5, and targeting the cortex yields the lowest transmittance from slightly greater than l=5 onward. The overall transmission range achieved is about 20%.

Figure 6:
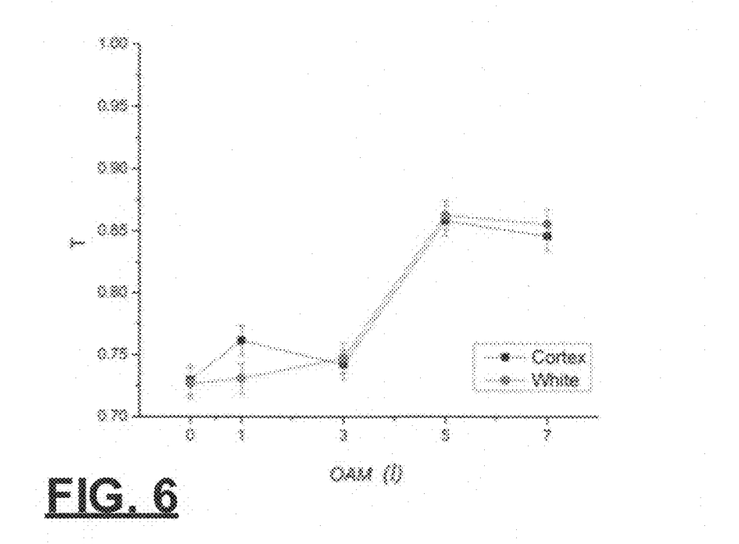
FIG. 6 is a graph of transmittance (T) through a 600-μm sample as a function of OAM (C) for a collimated left circularly polarized LG beam.

FIG. 6 shows transmission difference between the cortex and white mater for a circularly polarized collimated LG beam as a function of OAM with the tissue thickness of 600 μm. FIG. 5 displays a similar, yet slightly weaker trend between l and transmittance, as the graphs in FIG. 5 and FIG. 6 share similar curvatures and both display that a slightly higher amount of transmittance is achieved when targeting white matter versus targeting the cortex (specifically from l=3 to l=7). The overall transmission range achieved is about 14%. In addition, left circular polarization shows a high transmission variation. This could be expected due to the interaction of the handedness of beam and the different values of the OAM, and due to its pure state nature.

Figure 7:
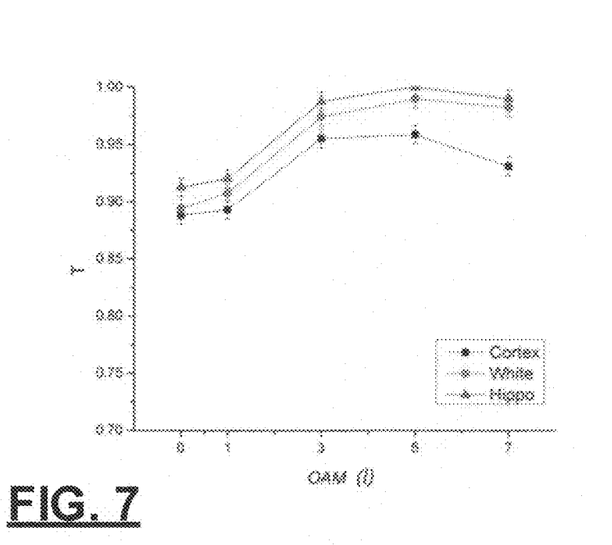
FIG. 7 is a graph showing Majorana transmittance (T) through a 120-μm sample as a function of OAM (C) for a collimated radially polarized LG beam.

The transmission in FIG. 7 shows difference between the cortex, white matter and hippocampus for a radially polarized collimated Majorana LG beam as a function of OAM with the tissue thickness of 120 μm. The transmittance of the LG beam consistently increases as l increases in all targeted regions and begins to wane as l approaches 7. The sharpest increase is experienced from l=0 to l=3. Targeting the hippocampus consistently yields the highest transmittance while targeting the cortex consistently yields the lowest transmittance. The overall transmission range achieved is about 12%.

Figure 8:
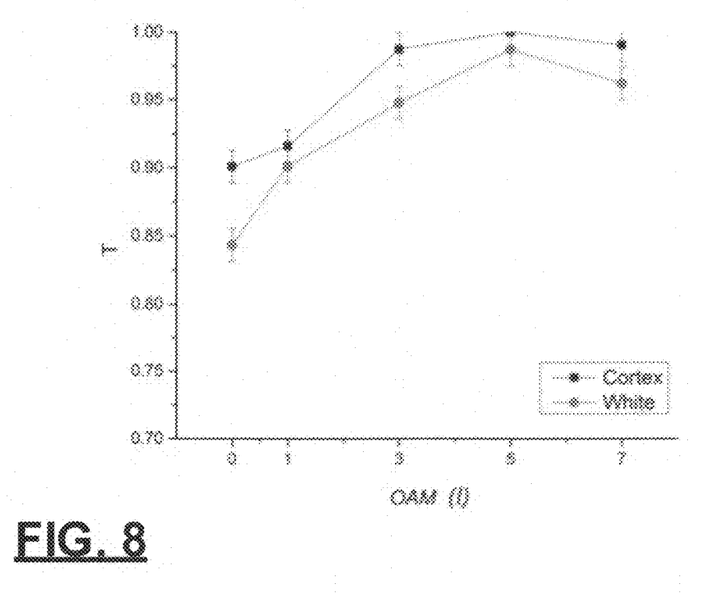
FIG. 8 is a graph showing Majorana transmittance (T) through a 600-μm sample as a function of OAM (C) for a collimated radially polarized LG beam.

FIG. 8 shows transmission difference between the cortex and white matter for a radially polarized collimated LG beam as a function of OAM with the tissue thickness of 600 gm. It shows a similar positive relationship between t and the transmittance. Also the cortex shows a greater transmission than white matter. The overall transmission range achieved is about 16%.

Moreover, radial polarization shows a high transmission range and well defined trend for each of the targeted regions. This is also expected due to the fact that radial is a superposition of left and right circular polarization.

Figure 9:
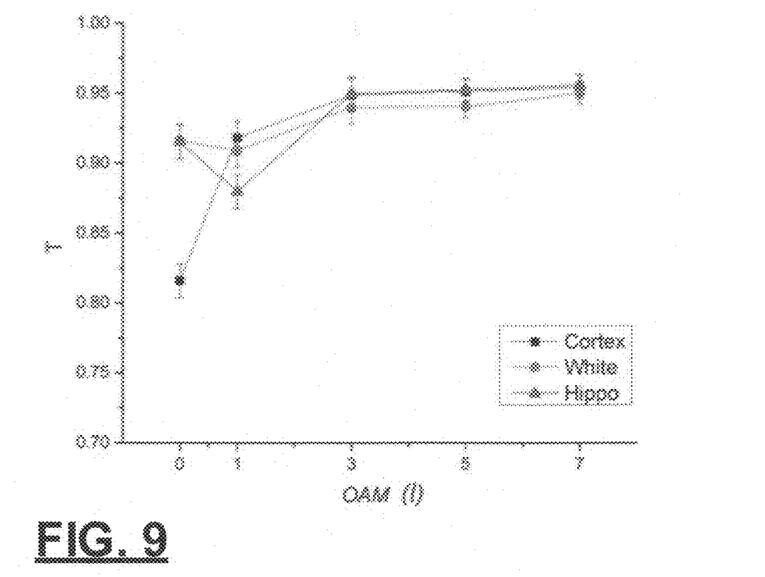
FIG. 9 is a graph showing Majorana transmittance (T) through a 120-μm sample as a function of OAM (C) for a collimated azimuthally polarized LG beam.

FIG. 9 shows transmission difference between the cortex, white matter and hippocampus for azimuthally polarized collimated LG beam as a function of OAM with the tissue thickness of 120 gm. The transmittance of the beam increases from l=1 to l=7. One difference that can be seen in all three regions is that from l=0 to l=1, only the transmittance for the cortex increases, while the transmittance for the white matter and hippocampus decreases. The overall transmission range achieved is about 14%.

Figure 10:
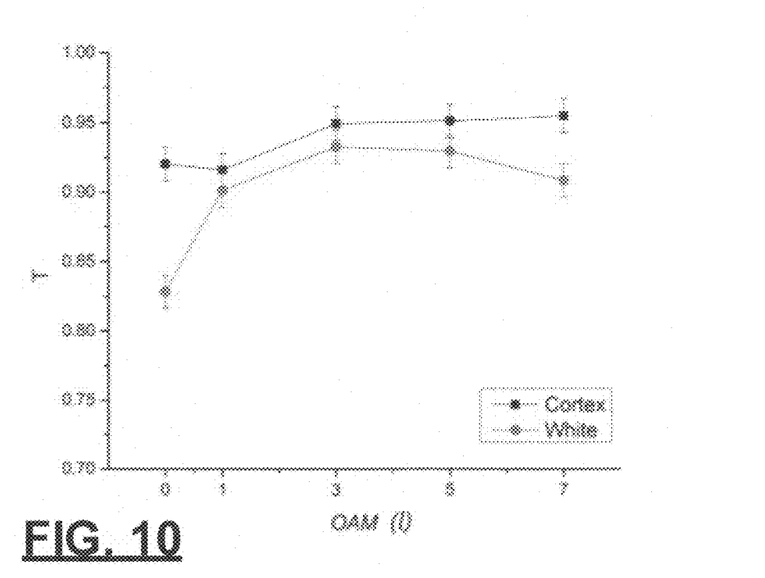
FIG. 10 is a graph showing Majorana transmittance (T) through a 600-μm sample as a function of OAM (C) for a collimated azimuthally polarized LG beam.

FIG. 10 shows transmission difference between the cortex and white matter for azimuthally polarized collimated LG beam as a function of OAM with the tissue thickness of 600 μm. This figure shows a constantly higher transmission for cortex with respect to the l values. In the case of white matter, the transmittance only increases from l=0 to l=3, after that the transmittance goes down. The overall transmission range achieved is about 13%. Additionally, azimuthal polarization shows a high overall transmission. Just like in the radial polarization case, this is also expected for azimuthal, being that is also made of left and right circular polarization.

The vortex beam produced the salient outcome that the transmittance of LG beams through brain tissue displays strong positive dependency on OAM for collimated, radially, azimuthally and left circularly polarized LG beams.

The Majorana beams of radial, azimuthal and linear polarization gave the highest transmission and less variation with OAM. However, the left circular polarization showed a large variation as the l values increase due to the fact of being a pure circular polarization state. The vector beams showed less variation with the l values, this is due to their non-separability and dual chirality nature. Moreover, vector beams gave clear trends when targeting different areas of the brain at the ballistic and diffusive region. Radial polarization gave the highest transmission range at the diffusive region, while left circular polarization showed the highest transmission for the ballistic region. Moreover, in targeting the hippocampus, cortex, and white matter, radially polarized light proved to be the most effective. Hence, these results support the idea that light transmission through different areas of the brain varies.

Moreover, these results allow for the optimization of optical brain imaging depending on which brain region is being targeted. For example, by targeting specific regions affected by neurodegenerative diseases, we are able to understand and learn more about the mystery behind these diseases with the aim of preventing or treating it. Also, the use of this imaging method at different brain regions will differentiate an abnormal brain tissue from a normal one. For a future project we plan to do brain transmission and imaging on a human brain with Alzheimer's disease, focusing on areas that are mainly affected such as hippocampus, cingulate gyrus, and amygdala. In addition, Forbes and Andrews showed dipole and quadrupole have a chiroptical effect associated with OAM with circular dichroism (left and right circular polarization). Afanasev and colleagues have shown that higher multipole transitions exhibit circular dichroism with OAM (l) dependency, in non-chiral atomic matter.

In conclusion, the radial and azimuthal, which are non-separately mixed photon states, and linear polarized beams are shown to be Majorana photons, shown in lKet>Dirac notations. A Majorana photon has within itself both direction of time and right and left handed twists; recapping that the photon and antiphoton are identical 1. These special entangled Majorana photon modes may be at the heart of the future optical and quantum computers as Majorana quasi photon qubits store and transfer information with less scattering and interference from the environment.

The disclosed system finds applications in two-photon fluorescence (TPF) imaging, second harmonic generation (SHG) imaging, third harmonic generation (THG) imaging and nonlinear optical (NLO) imaging. Imaging depth can be, for example, 1 μm to 1000 μm or, in other embodiments, multiple centimeters in depth. The wavelength of light may be, for example, a wavelength between 650 nm to 950 nm (NIR window), 1000 nm to 2500 nm (SWIR window) or 1600 to 1870 nm (golden window).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for imaging a biological tissue sample, the method comprising:
   transmitting Majorana photons through the biological tissue sample, wherein the Majorana photons have a circular polarization, a radial polarization or an azimuthal polarization, thereby producing transmitted Majorana photons;
   receiving the transmitted Majorana photons with an optical receiver, thereby producing a received signal;
   processing the received signal to produce a digital image of the biological tissue sample.

2. The method as recited in claim 1, wherein the biological tissue sample is a brain tissue sample.

* * * * *